United States Patent [19]

Carville

[11] Patent Number: 4,699,132

[45] Date of Patent: Oct. 13, 1987

[54] PATIENT RESTRAINT DEVICE

[76] Inventor: Robin K. Carville, Rte. 2, Box 78, Victoria, Tex. 77901

[21] Appl. No.: 872,155

[22] Filed: Jun. 9, 1986

[51] Int. Cl.$^4$ .................. A61F 13/00; A47C 27/08
[52] U.S. Cl. ........................ 128/134; 128/DIG. 15; 5/424
[58] Field of Search ............. 5/424, 494; 128/133, 128/134, DIG. 15; 272/145, 900, 143; 273/DIG. 30

[56] References Cited

U.S. PATENT DOCUMENTS

| 837,373 | 12/1906 | Akers | 5/424 X |
|---|---|---|---|
| 2,843,858 | 7/1958 | Bjorklund | 272/900 X |
| 3,100,484 | 8/1963 | Berl | 128/134 |
| 3,474,781 | 10/1969 | Gaylord, Jr. | 5/494 X |
| 3,524,643 | 8/1970 | Hazelitt, Sr. | 272/900 |
| 3,536,357 | 10/1970 | Murcott | 128/134 X |
| 3,779,540 | 12/1973 | Boudreau | 5/424 X |
| 3,897,778 | 8/1975 | Forbes-Robinson et al. | 128/134 |
| 4,069,813 | 1/1978 | Gilula | 128/133 X |
| 4,602,782 | 7/1986 | Carlson | 272/900 X |
| 4,608,973 | 9/1986 | Green et al. | 128/134 |

FOREIGN PATENT DOCUMENTS 0871943  2/1953  Fed. Rep. of Germany ...... 128/133

Primary Examiner—Robert A. Hafer
Assistant Examiner—Kathleen J. D'Arrigo

[57] ABSTRACT

A Patient Restraint Device that allows medical and rescue personnel to quickly immobilize and secure an injured person to a stretcher, cot or backboard. The invention utilizes a compact, rapid deployment configuration and features "J" shaped clips to attach restraining straps to the stretcher side rails or edges, and a length adjusting device to quickly tighten or loosen the restraining strap.

2 Claims, 5 Drawing Figures 4,699,132

PATIENT RESTRAINT DEVICE

BACKGROUND OF THE INVENTION

1. Field of the Invention

The invention relates to a device used by medical and rescue personnel for rapidly immobilizing and securing an injured person to a stretcher, cot, backboard or similar apparatus, by means of an adjustable strap that "clips" to the edges or side rails of the particular stretcher apparatus.

2. Description of Prior Art

The restraint straps currently in use generally fall into two categories. In the first category are straps that are passed beneath the stretcher and completely encircle the patient and the stretcher. These straps are either left in place on the stretcer when not in use or they are stored separately until needed. If they are left in place, they must be released or loosened before placing a patient on the stretcher. The loose ends often become entangled while the stretcher is being positioned under the patient and the strap ends frequently become lodged under the stretcher after the patient is in place. Straps left attached to stretchers and backboards stored in narrow slots or compartments on rescue vehicles tend to snag on interior projections; and because overall board width (with straps and accompanying buckles) is increased, usable space for additional stretchers and backboards is reduced. If the straps are removed from stretchers and stored separately, they are not only bulky and time consuming to unwrap, they also must be re-routed under the stretcher or backboard before the patient is placed on it.

In the second category are straps that are semi-permanently attached to the edgess or side rails of the stretcher or backboard, rather than passing completely beneath and around it. These straps have many of the same entanglement problems as those in the first category, and they hamper safe effective immobilization because the straps can't be moved along the edge or side rail to accommodate the wide range of patient sizes and shapes. Also included in this category are makeshift or improvised straps such as cloth cravats that must be tied to the side rails or thru hand hold slots in the stretcher. These makeshift straps are not only limited by the availability of attachment points, they have no provision for quickly adjusting the length. They must be untied, readjusted and retied.

All of the previously mentioned types and methods of patient restraint have at least one major problem in common; they all cause unnecessary delay in immobilizing and securing injured persons when time is extremely important. My invention virtually eliminates the problems previously mentioned and dramatically reduces the time necessary to safely and effectively restrain injured persons to a stretcher.

SUMMARY OF THE INVENTION

The invention relates to a patient restraint device that is extremely compact in its packaged configuration and can be deployed rapidly, from that configuration. It comprises a means to quickly clip or hook a strap end to the side rail or edge of stretchers, cots, and backboards at any point along its rail or edge. The position of the strap, along the edge of the stretcher, is not limited to available slots, hand holds or attachment hardware. The straps can be quickly and easily attached at any point, even after the patient is in place on the stretcher.

It is the object of this invention to enable the medic or rescuer to strategically place the patient restraint strap for the most effective immobilization, to provide a single versatile restraint for a wide variety of stretcher types and medical situations and to dramatically reduce the time necessay to package an injured patient for transport to definitive medical care.

DESCRIPTION OF PREFERRED EMBODIMENT

Figure 1:
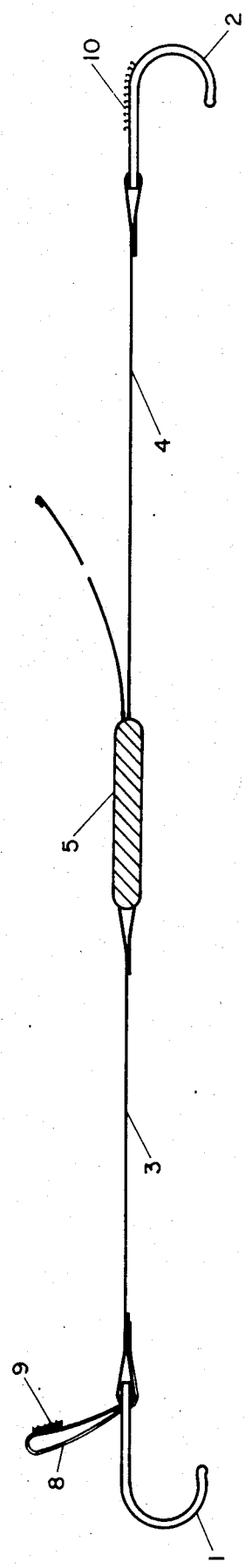
FIG. 1 is a ½ scale front view of an embodiment of the Patient Restraint Device.
Figure 2:
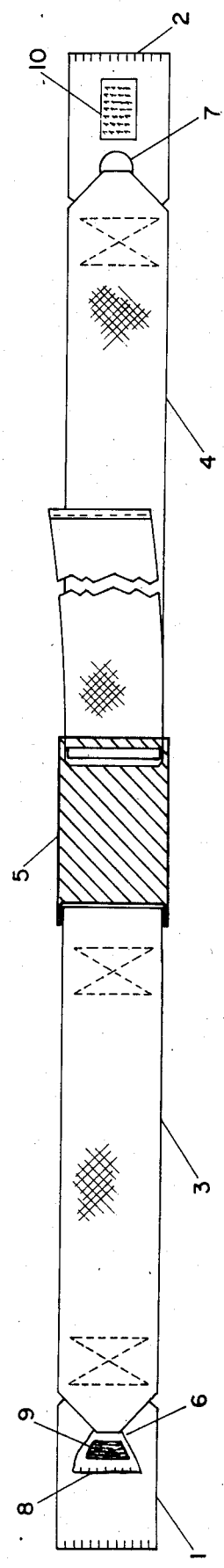
FIG. 2 is a ½ scale top view of the embodiment of the Patient Restraint Device.

Referring to FIGS. 1 thru 5, an embodiment of the Patient Restraint Device invention is illustrated that depicts all of the elements of the invention and their relationship with each other. In FIGS. 1 and 2, the "J" shaped clips 1 and 2 are attached to lengths of strap material 3 and 4, by means of openings 6 and 7 formed at the straight end of the "J" shaped clips. One end of the shorter strap material 3 is attached to a length adjusting device 5. The ends of a section of loop tape 8 are fixed to the strap material 3 at its connection to the clip 1. The loop tape 8 passes thru the formed opening 6 in the clip 1. A section of VELCRO pile fabric 9 is attached to the loop portion of the tape 8.

One end of the longer strap material 4 passes thru the length adjusting device 5, providing a means of altering the length of the Patient Restraint Device and a means of tightening the device around a patient. The opposite end of the longer strap material 4 is attached to the second "J" shaped clip 2. A section of VELCRO hook fabric 10 is fixed to the second "J" shaped clip 2.

Figure 3:
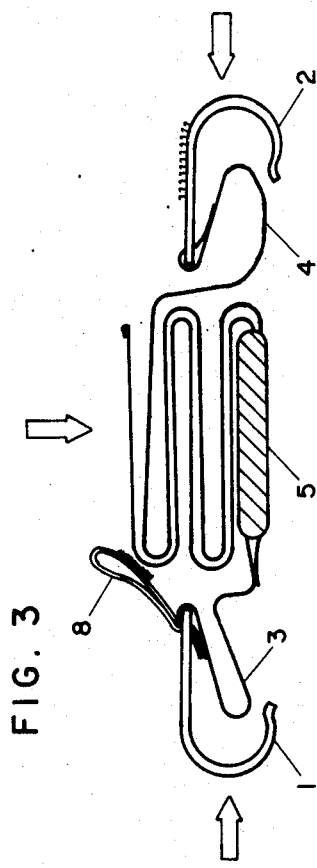
FIG. 3 is a ½ scale front view of the embodiment of the Patient Restraint Device illustrating the folding method that will result in the packaged configuraion.

Referring to FIG. 3, the method of folding and positioning the strap material 3 and 4 is illustrated. This method of folding and positioning the strap material allows the Patient Restraint Device to be reduced to a small compact form, thereby protecting the strap material from abrasion and tangling while being stored, and still allows simple rapid deployment by merely pulling the two "J" shaped clips away from each other.

Figure 4:
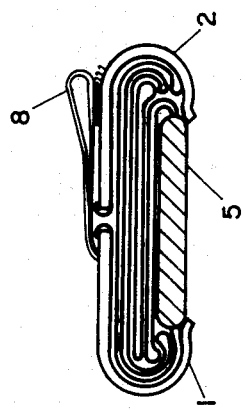
FIG. 4 is a ½ scale front view of the embodiment of the Patient Restraint Device in its packaged configuration.

Referring to FIG. 4, the Patient Restraint Device is in its packaged configuration. The loop tape 8, with VELCRO pile fabric attached, passes thru the formed opening 6 in the "J" shaped clip 1, and is pressed against the VELCRO hook fabric 10 on second clip 2, thereby fastening the loop tape 8 to clip 2. While fastened, the loop 8 prevents separation of clips 1 and 2. In the packaged configuration, the ends of the curved ends of the J-shaped clips are separated by a distance which is less than the length of the length adjusting device, 5. The strap material 3 and 4 fills the void inside the clips 1 and 2 and the strap adjusting device, thereby providing form and support for the packaged configuration of the Patient Restraint Device.

Figure 5:
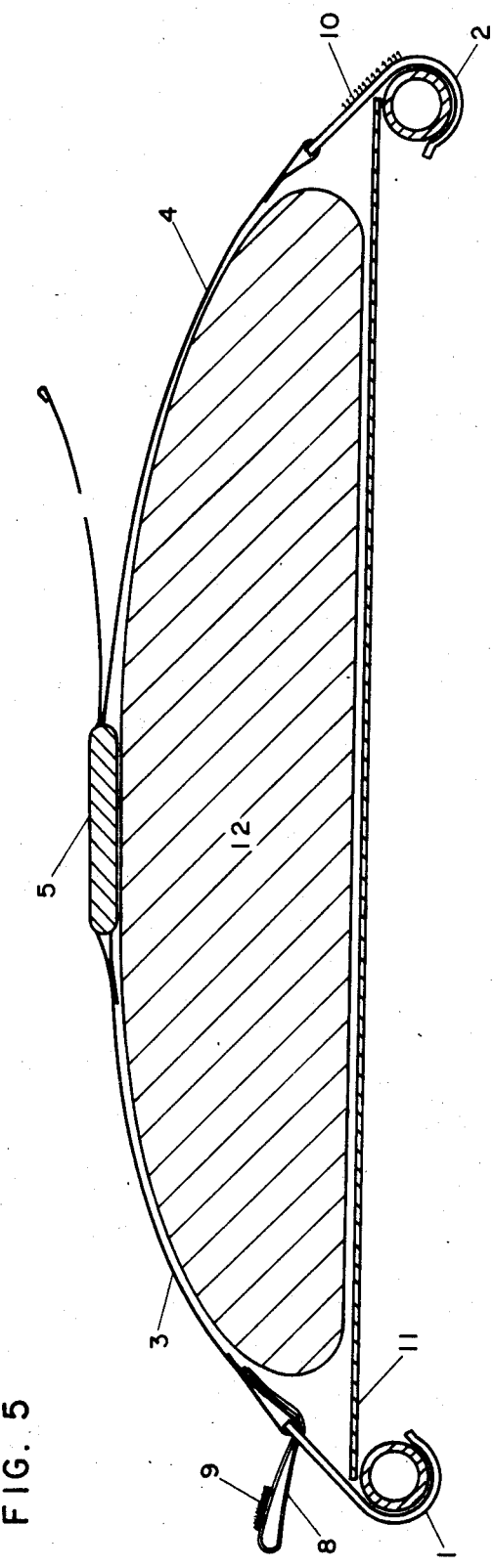
FIG. 5 is a ½ scale front view illustrating the deployed configuration of the Patient Restraint Device applied to a stretcher apparatus.

Referring to FIG. 5, the Patient Restraint Device is illustrated in the deployed configuration. The two "J" shaped clips 1 and 2 are clipped over the edges of a stretcher apparatus 11. The loose end of the strap material 4 may be pulled to shorten and thereby tighten the strap around the patient 12.

Although only one detailed embodiment of the invention is illustrated in the drawings and previously described in detail, this invention contemplates any configuration and design of components which will accomplish the equivalent result. As an example, the invention could incorporate a clip that has right angle bends rather than a smooth curve, so that it may better attach to squared edges of some stretchers. As another example, the securing element could be comprised of elastic material, a mechanical snap or a latch to secure the clips. As a further example, the clips, the strap material and the length adjusting device could be of various widths, materials and thicknesses provided they are consistent in proportion to each other so that the function and merits of the invention are not significantly affected.

I claim:

1. A Patient Restraint Device, for the purpose of rapidly securing and immobilizing an injured person to a stretcher apparatus in order to minimize patient movement as quickly and effectively as possible and thereby prevent further injury, comprising
   a. a pair of "J" shaped clips, each of said clips being formed from flat rigid band material resulting in a straight end and a curved end, said straight end having a formed opening, said curved end being of sufficient inside circumference and formed so as to engage the lateral edges of a stretcher apparatus, and said clips being preferably one inch to four inches wide,
   b. flexible strap material attached to both said clips by means of said formed openings in said clips and extended therebetween, the width of said strap material being approximately the same as that of said clips, said strap material being sufficient in length to extend from one side of a stretcher apparatus, across an injured person to the opposite side of said stretcher apparatus,
   c. a length adjusting device attached to said strap material and located medial to said two clips, whereby the length of said strap material may be adjusted to accomodate varying sizes of an injured person and to provide means to tighten said strap material against said injured person, thereby minimizing movement of said person relative to said stretcher apparatus, and the width of said length adjusting device being preferably the same approximate width as said clips,
   d. a securing element attached to the straight end of said clips, said securing element providing means to hold said clips in a relative position whereby the concavity of said curved ends of said clips are facing inward and the distance between the ends of the curved ends is less than the length of the length adjusting device so that the device maintains a compact easily storable package.

2. The method of positioning the elements of the Patient Restraint Device described in claim 1 whereby the "J" shaped clips and the length adjusting device contain and protect the flexible strap material folded within the cavity formed by said method of positioning, and said method of positioning facilitates rapid deployment of said patient restraint device without the need to unwrap or untangle said flexible strap material, said method comprising the steps of
   a. folding the flexible strap material parallel and adjacent to one side of the length adjusting device whereby the folds in said strap are approximately the same length as said length adjusting device,
   b. compressing said folds of said strap against said side of said length adjusting device,
   c. sliding the "J" shaped clips over the ends of said folds and length adjusting device,
   d. engaging the securing element, thereby holding said elements of said patient restraint device in position described.

* * * * *